US00PP35301P2

(12) United States Plant Patent
Koot

(10) Patent No.: US PP35,301 P2
(45) Date of Patent: Aug. 8, 2023

(54) ***CROSSANDRA* PLANT NAMED 'DOCROSWAT'**

(50) Latin Name: *Crossandra infundibuliformis*
Varietal Denomination: Docroswat

(71) Applicant: DUMMEN GROUP B.V., De Lier (NL)

(72) Inventor: Arjan Koot, Oeffelt (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 18/072,132

(22) Filed: Nov. 30, 2022

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05); *A01H 5/02* (2013.01)

(58) Field of Classification Search
USPC ..... Plt./263.1
CPC ..... A01H 6/00; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Crossandra* plant named 'Docroswat', characterized by its compact, upright to outwardly spreading plant habit; moderately vigorous and moderate growth rate; freely branching habit; dense and bushy plant form; freely flowering habit; reddish orange-colored flowers; and good garden performance.

1 Drawing Sheet

Botanical designation: *Crossandra infundibuliformis.*
Cultivar denomination: 'DOCROSWAT'.

BACKGROUND OF THE INVENTION

The present invention relates to a new and distinct cultivar of *Crossandra* plant, botanically known as *Crossandra infundibuliformis*, and hereinafter referred to by the name 'Docroswat'.

The new *Crossandra* plant is a product of a planned breeding program conducted by the Inventor in De Lier, The Netherlands. The objective of the breeding program is to create new compact and freely-branching *Crossandra* plants with numerous attractive flowers.

The new *Crossandra* plant originated from an open-pollination in September, 2018 in De Lier, The Netherlands of *Crossandra infundibuliformis* 'Nile Queen', not patented, as the female, or seed, parent with an unknown selection of *Crossandra infundibuliformis* as the male, or pollen, parent. The new *Crossandra* plant was discovered and selected by the Inventor as a single flowering plant from within the progeny of the stated open-pollination in a controlled greenhouse environment in De Lier, The Netherlands in July, 2019.

Asexual reproduction of the new *Crossandra* plant by terminal cuttings in a controlled greenhouse environment in De Lier, The Netherlands since July, 2019 has shown that the unique features of this new *Crossandra* plant are stable and reproduced true to type in successive generations.

SUMMARY OF THE INVENTION

Plants of the new *Crossandra* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Docroswat'. These characteristics in combination distinguish 'Docroswat' as a new and distinct *Crossandra* plant:

1. Compact, upright to outwardly spreading plant habit.
2. Moderately vigorous and moderate growth rate.
3. Freely branching habit; dense and bushy plant form.
4. Freely flowering habit.
5. Reddish orange-colored flowers.
6. Good garden performance.

Plants of the new *Crossandra* can be compared to plants of the female parent selection. Plants of the new *Crossandra* differ primarily from plants of the female parent selection in the following characteristics:

1. Plants of the new *Crossandra* are more compact than plants of the female parent selection.
2. Plants of the new *Crossandra* have shorter internodes than plants of the female parent selection.
3. Leaves of plants of the new *Crossandra* are glossier than leaves of plants of the female parent selection.
4. Flowers of plants of the new *Crossandra* are reddish orange in color whereas flowers of plants of the female parent selection are red in color.

Plants of the new *Crossandra* can be compared to plants of *Crossandra infundibuliformis* 'Orange Marmalade', not patented. In side-by-side comparisons, plants of the new *Crossandra* differ primarily from plants of 'Orange Marmalade' in flower color as flowers of plants of the new *Crossandra* are reddish orange in color whereas flowers of plants of 'Orange Marmalade' are orange in color. In addition, leaves of plants of the new *Crossandra* are lighter green in color than leaves of plants of 'Orange Marmalade'.

BRIEF DESCRIPTION OF THE PHOTOGRAPH

The accompanying colored photograph illustrates the overall appearance of the new *Crossandra* plant showing the colors as true as it is reasonably possible to obtain in colored reproductions of this type. Colors in the photograph may differ slightly from the color values cited in the detailed botanical description which accurately describe the actual colors of the new *Crossandra* plant. The photograph is a side perspective view of a typical flowering plant of 'Docroswat' grown in a container.

DETAILED BOTANICAL DESCRIPTION

The aforementioned photograph and following observations and measurements describe plants grown during the summer in 12-cm containers in a glass-covered greenhouse in De Lier, The Netherlands and under cultural practices typical of commercial *Crossandra* production. During the production of the plants, day temperatures ranged from 20° C. to 35° C. and night temperatures ranged from 17° C. to 25° C. Plants were pinched one time about five weeks after sticking unrooted cuttings. Plants were 14 weeks old when the photograph was taken and twelve weeks old when the description was taken. In the following description, color references are made to The Royal Horticultural Society Colour Chart, Fifth Edition, except where general terms of ordinary dictionary significance are used.

Botanical classification: *Crossandra infundibuliformis* 'Docroswat'.

Parentage:

*Female, or seed, parent.*—*Crossandra infundibuliformis* 'Nile Queen', not patented.

*Male, or pollen, parent.*—Unknown selection of *Crossandra infundibuliformis*, not patented.

Propagation:

*Type.*—By terminal cuttings.

*Time to initiate roots, summer.*—About seven to ten days at temperatures about 26° C. to 28° C.

*Time to initiate roots, winter.*—About 12 to 14 days at temperatures about 16° C. to 18° C.

*Time to develop roots, summer.*—About 21 to 24 days at temperatures about 26° C. to 28° C.

*Time to develop roots, winter.*—About 26 to 30 days at temperatures about 16° C. to 18° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Compact, upright to outwardly spreading plant habit; moderately vigorous and moderate growth rate.

*Branching habit.*—Freely branching habit with about three primary lateral branches each with about two to three secondary laterals; bushy and dense plant form.

*Plant height, soil level to top of foliar plane.*—About 25 cm.

*Plant height, soil level to top of floral plane.*—About 31 cm.

*Plant diameter* (*area of spread*).—About 55 cm.

Lateral branch description:

*Length.*—About 26 cm.

*Diameter.*—About 8 mm.

*Internode length.*—About 8.5 cm.

*Texture and luster.*—Smooth, glabrous; glossy.

*Strength.*—Moderately strong, flexible.

*Color, developing.*—Close to 146A.

*Color, fully developed.*—Close to 146A; at the internodes, close to 146B.

Leaf description:

*Arrangement.*—Whorled, simple.

*Length.*—About 6 cm to 8 cm.

*Width.*—About 2 cm to 3 cm.

*Shape.*—Lanceolate.

*Apex.*—Acute.

*Base.*—Cuneate.

*Margin.*—Entire.

*Texture and luster, upper surface.*—Smooth, glabrous; glossy.

*Texture and luster, lower surface.*—Smooth, glabrous; semi-glossy.

*Venation pattern.*—Pinnate.

*Color.*—Developing leaves, upper surface: Close to 143A. Developing leaves, lower surface: Close to 144B. Fully developed leaves, upper surface: Close to 146A; venation, close to N147A. Fully developed leaves, lower surface: Close to 144A; venation, close to N144C.

*Petioles.*—Length: About 1.5 cm. Diameter: About 3 mm. Strength: Moderately strong. Texture and luster, upper and lower surfaces: Smooth, glabrous; semi-glossy. Color, upper surface: Close to 146A. Color, lower surface: Close to 144A.

Flower description:

*Flower type and habit.*—Salverform flowers arranged on terminal racemes; freely flowering habit with about 14 to 20 flowers per inflorescence and about 292 flowers developing per plant during the flowering season; flowers face mostly upright to outwardly.

*Natural flowering season.*—Plants flower continuously during the summer in The Netherlands; plants begin flowering about eight to ten weeks after planting.

*Flower longevity.*—Flowers last about two to four weeks on the plant depending on temperature; flowers not persistent.

*Fragrance.*—None detected.

*Inflorescence height.*—About 8 cm to 9 cm.

*Inflorescence diameter.*—About 6 cm to 8 cm.

*Flower buds.*—Length: About 1.5 cm. Diameter: About 4 mm. Shape: Conical. Texture and luster: Smooth, glabrous; matte. Color: Close to 35B.

*Flower diameter.*—About 2.5 cm by 4.5 cm.

*Throat diameter.*—About 2 mm.

*Tube length.*—About 3 cm.

*Tube diameter.*—About 2 mm.

*Petals.*—Quantity and arrangement: Corolla consists of three to five petals in a single whorl and fused towards the base. Lobe length: About 2.2 cm. Lobe width: About 1.3 cm. Lobe shape: Roughly fan-shaped. Lobe apex: Rounded. Lobe margin: Entire; not undulate. Lobe texture and luster, upper and lower surfaces: Smooth, glabrous; matte. Throat texture: Smooth, glabrous. Tube texture: Smooth, glabrous. Color: When opening, upper surface: Close to 35A. When opening, lower surface: Close to 35B. Fully opened, upper surface: Close to 35A; venation, close to 35A; color becoming closer to 31B with subsequent development. Fully opened, lower surface: Close to 35C; venation, close to 35B; color becoming closer to 31C with subsequent development. Throat: Close to 12A; venation, close to 4C. Tube: Close to 12B; venation, close to 12C.

*Sepals*.—Quantity and arrangement: About three per flower in an infundibuliform calyx. Length: About 6 mm. Width: About 3 mm. Shape: Lanceolate. Apex: Acute. Base: Acuminate. Margin: Entire. Texture and luster, upper and lower surfaces: Slightly pubescence; matte. Color, upper and lower surfaces: Close to 143C.

*Flower bracts*.—Quantity: One to three per flower. Length: About 1 cm to 3 cm. Width: About 1.5 cm. Shape: Conical. Texture, upper and lower surfaces: Pubescent. Color, upper and lower surfaces: Close to 146A.

*Peduncles*.—Length: About 9.5 cm. Diameter: About 3 mm. Angle: Upright to outwardly spreading. Strength: Strong, flexible. Texture and luster: Smooth, glabrous; glossy. Color: Close to 143A.

*Pedicels*.—Length: About 5 cm to 6 cm. Diameter: About 2 mm. Angle: Upright to outwardly spreading. Strength: Moderately strong, flexible. Texture and luster: Smooth, glabrous; semi-glossy. Color: Close to N144A.

*Reproductive organs*.—Androecium: Stamen number: One per flower. Filament length: About 1.5 cm. Filament color: Close to N199C. Anther length: About 2 mm to 3 mm. Anther width: Less than 1 mm. Anther color: Close to 15A. Amount of pollen: Scarce. Pollen color: Close to 15A. Gynoecium: Pistil number: One per flower. Pistil length: About 2 cm to 3 cm. Style length: About 2 cm to 3 cm. Style color: Close to N199C. Stigma shape: Rounded. Stigma color: Close to 16A. Ovary color: Close to 143C.

*Seeds and fruits*.—To date, seed and fruit development has not been observed on plants of the new *Crossandra*.

Garden performance: Plants of the new *Crossandra* have been observed to have good garden performance and tolerate temperatures from about 10° C. to about 45° C.

Pathogen & pest resistance: To date, plants of the new *Crossandra* have not been shown to be resistant to pathogens and pests common to *Crossandra* plants.

It is claimed:

1. A new and distinct *Crossandra* plant named 'Docroswat' as illustrated and described.

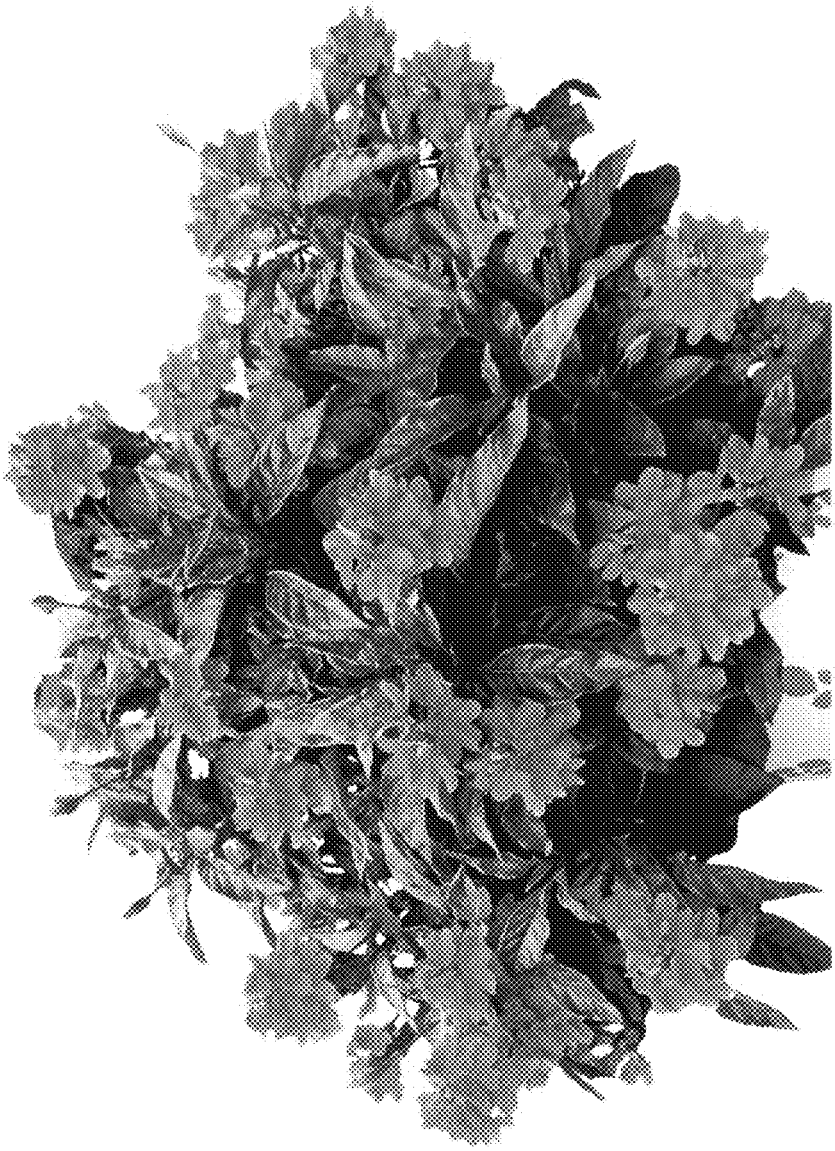

* * * * *